United States Patent [19]
Misawa et al.

[11] Patent Number: 5,393,957
[45] Date of Patent: Feb. 28, 1995

[54] LASER MICROPROCESSING AND THE DEVICE THEREFOR

[75] Inventors: Hiroaki Misawa; Keiji Sasaki, Kyoto; Masanori Koshioka, Leopalesu 3-201, 1-66 Sagano Arisugawa, Ukyo-Ku, Kyoto-shi, Kyoto; Noboru Kitamura, Kyoto; Hiroshi Masuhara, Osaka, all of Japan

[73] Assignees: Research Development Corporation of Japan; Masanori Koshioka, Japan

[21] Appl. No.: 987,594

[22] Filed: Dec. 9, 1992

Related U.S. Application Data

[62] Division of Ser. No. 623,615, Dec. 7, 1990.

[30] Foreign Application Priority Data

Dec. 7, 1989 [JP] Japan ................ 1-318258
Dec. 7, 1989 [JP] Japan ................ 1-318259
Mar. 27, 1990 [JP] Japan ................ 2-78421

[51] Int. Cl.[6] .......................................... B23K 26/00
[52] U.S. Cl. ........................... 219/171.85; 219/121.76
[58] Field of Search .................... 219/121.26, 121.85

[56] References Cited

U.S. PATENT DOCUMENTS

| | | | |
|---|---|---|---|
| 4,200,669 | 4/1980 | Schaefer et al. | 427/121.67 |
| 4,277,305 | 7/1981 | Bohachevsky | 176/1 |
| 4,290,847 | 9/1981 | Johnson et al. | 176/1 |
| 4,579,750 | 4/1986 | Bowen et al. | 427/53.1 |
| 4,707,584 | 11/1987 | Kimbara | 215/121.67 |
| 4,789,770 | 12/1988 | Kasner et al. | 215/121.7 |
| 4,839,497 | 6/1989 | Sankar et al. | 215/121.71 |
| 4,871,251 | 10/1989 | Preikschat et al. | 356/336 |
| 4,925,523 | 5/1990 | Braren et al. | 215/121.69 X |
| 4,987,286 | 1/1991 | Allen | 215/121.68 |

OTHER PUBLICATIONS

Misawa, H. et al., "Chemistry Letters", 1479–1482 (1990).
Misawa, H. et al., "J. Am. Chem. Soc.", 113, 7859–7863 (1991).
Ashkin, A., "Science", 210(4474) 1081–1088 (Dec. 5, 1980).

Primary Examiner—C. L. Albritton
Attorney, Agent, or Firm—Wenderoth, Lind & Ponack

[57] ABSTRACT

The present invention provides microprocessing and the device therefor which is characterized by radiating proessing pulse laser together with trapping laser to perform the modification and processing of particles and micropcapsules.

In the case of using such method for implosion, the reaction group is caused to be released by imploding the micro capsule with the reactive goup enclosed to implosion, permitting specified reaction and processing.

4 Claims, 5 Drawing Sheets

LASER MICROPROCESSING AND THE DEVICE THEREFOR

This is a Rule 60 Divisional application of Ser. No. 07/623,615, filed on Dec. 7, 1990.

FIELD OF THE INVENTION

The present invention relates to laser microprocessing and the device therefor. More particularly, it relates to laser microprocessing and the device therefor which permits easy and accurate chemical modification and processing of the surface of a particle or a microcapsule through the radiation of laser beams, and further to a fine processing using these particles and microcapsule and the application thereof in the field of electronics, chemical engineering or medicine, etc.

PRIOR ART

During recent years, attention has been focused on the development of fine modification and microprocessing technology thereof of chemical materials, such as high-molecular weight materials and inorganic substances, on a particle level. And aggressive research and development work has been in progress on this subject in the hope that such technology will be able to manipulate the elementary process of conversion process. Also in living cells, microprocessing designed to perform the transplantation, migration, fusion and other fine manipulation thereof has become very important.

Conventionally, various methods by chemical manipulations have been proposed for such microparticle. But with chemical methods, it was exceedingly difficult to control the reaction between particles to be processed and reaction processing agent, and there was a limit in precision to performing manipulations of particles one by one.

On the other hand, in the field of manipulation of living cells, it has been possible to perform migration process by manual methods, such as fine injection process, and hence it has become possible to improve manifestation efficiency to approximately $10^2$. However, by this method, the manipulator performs the processing by bringing a micropipette in direct contact with individual cells under a microscope. Hence, it becomes indispensable for such processing to be made within a clean bench, and such processing cannot be made automatic. For this reason, processing efficiency and processing amount depend on the skill and labor of the manipulator, and it is difficult to perform accurate processing in a short duration of time.

As an alternative to the conventional method as described above, the processing method using laser beams to perform the micro manipulation of particles has been proposed.

Laser light is excellent in homogeneousness, directivity, luminance and controllability. And hence light energy can be concentrated and radiated on the fine regions of particles, and it becomes possible to perform non-contact accurate localized microprocessing which has been impossible by the conventional method.

For instance, as a cell processing method using laser beams, a method has been proposed for collecting Ar laser beams with a system of lenses, adjusting the portion of particles to be irradiated on with the locating device of the microscope stage and radiating the same. The effect on cells and other particles can be varied by varying the wavelength of laser beams to be radiated, and hence attempts are being made to use laser beams.

As a fine processing method using laser beams, a pattern-transfer in which laser beams are radiated, on a substrate through a photomask is known as an important process in the semiconductor fields.

However, by the conventional methods, there have been limitations to the selection of radiation conditions, including the wavelength of laser beams, spot size diameter, pulse width and number of shots and a resolution as poor as on the order of micron can be expected. It was impossible, for this reason, to improve the precision of fine and microprocessing with laser beams.

By the conventional method, not much has been known about the radiation of laser beams and the behavior control of particles. For example, the technology for chemical modification and processing of particles has not been established, and the particle-locating precision been poor and far from practical.

SUMMARY OF THE INVENTION

The present invention has been made considering the foregoing circumstances, and has an objective of providing a new device which radiates laser beams onto particle sample as precisely as the order of micron, and the modification and processing of particles can be performed to a high precision.

To solve the above problems, this invention provides a microprocessing method and a device therefor which is characterized by radiating processing pulse laser together with trapping laser to perform the modification and processing of particles and microcapsules.

Furthermore, it also provides microprocessing which is characterized by shifting a microcapsule trapped by the radiation of laser beams and radiating processing laser beams for implosion, and by performing chemical modification and processing at required location with the reaction substrate released by said implosion, and provides a fine modification and processing device and the method therefor which is characterized by controlling processing laser energy to cause laser multiple photon reactions.

At the same time, this invention provides a microscopic microspectroscope which is characterized by being equipped with an excitation pulse laser as well as a trapping laser to determine the reaction characteristics and phenomena that provide the basis for these microprocessings, and provides a method for using this device.

DETAILED DESCRIPTION OF THE EMBODIMENTS

What we call phototrapping, one of the features of microprocessing of this invention attracts attention as one of the manipulations on particles, and uses outstanding coherent characteristics possessed by laser beams to transfer the momentum which light has as a dynamic momentum that exerts upon a body and applies force to particles to trap or shift the body.

By this phototrapping manipulation, only the force brought by laser beams exerts upon an object, making possible a fully non-contact and non-destructive manipulation.

In addition to such laser trap, the present invention uses a processing pulse laser.

This laser processing is designed to perform modification, processing and other manipulations to the trapped particles under the required conditions. The most typical and important manipulations in the invention include the decomposition, division, local conversion, and chemical modification of particles, the connection and fusion between particles, and crosslinking with functional reaction groups.

Great expectations are placed on this phototrapping technology as operations on particles.

Here is a description of the principle of phototrapping. Laser beams enter particles through a lens, and is reflected and refracted, and the momentum possessed by the laser is delivered to the particle. Since the reflection rate is normally low, the momentum delivered by refraction becomes prevailing, and the force exerted thereby is transmitted to the particle.

The particle is brought into being trapped by the laser. Accordingly, when the laser beam is caused to move, the particle follows the movement.

As is evident from this principle, the manipulations such as non-contact and non-destructive trapping and shifting of particles become possible, and if the particle, for instance, polmyer particles, on living cells and bacteria are subjected to modification and processing, this phototrapping becomes a very useful means in the reaction manipulation of particles.

One of the characteristic forms of the present invention adopts the foregoing laser beams trapping means.

Figure 1:
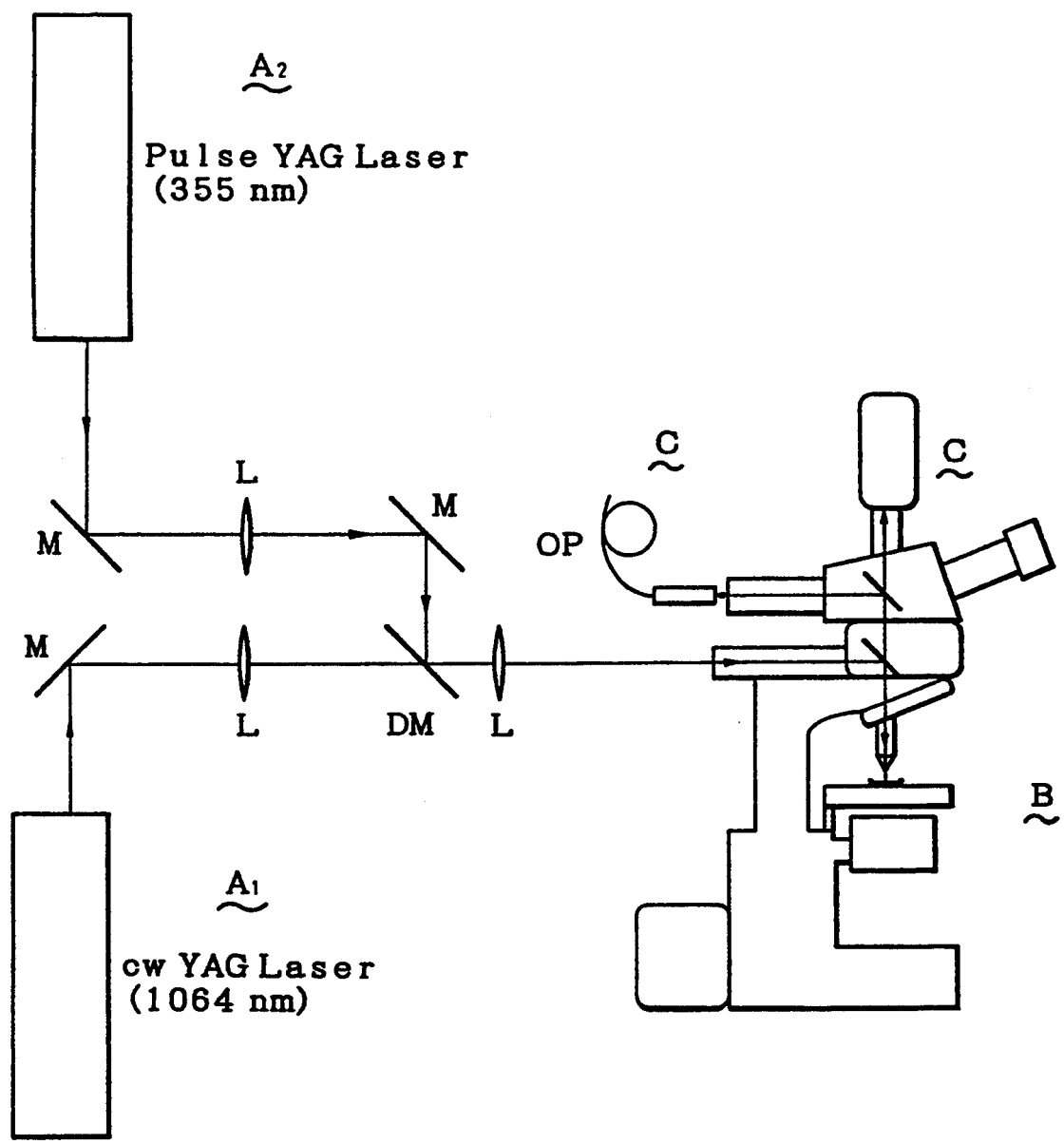
FIG. 1 is a block diagram of one example of the small-sized device for microprocessing according to the present invention.

FIG. 1 is a block diagram illustrating an example of a small-sized device for microprocessing according to the present invention.

As is shown in this figure, the device of the invention possesses laser devices ($A^1$) ($A^2$), fine positioning device of laser radiation protion (B) and an image processing device (C).

The laser device ($A^1$) constitutes a very compact phototrapping device as microscopic system. This device makes it possible to manipulate microparticles easily and smoothly.

The laser devices ($A^1$) ($A^2$) permit the selection of a laser source and the optical system thereof according to the type and size of particles involved and the purpose of necessary modification and/or processing.

The laser device ($A^2$) radiates a pulse laser beam which is used to provide modification end/or processing with the microcapsule trapped.

The processing laser implodes the trapped microcapsules, permitting the modification end processing under specified conditions.

By using such method of implosion, the reaction group is caused to be released by imploding the microcapsule with the reactive group enclosed to implosion, permitting specified reaction and processing.

It becomes possible, for example, to cause these reactions at the fine regions of surface substrate, and give treatment to the affected portions of a cancer by allowing medicine to release.

This invention is applicable to various particles, including organic polymer, the latex thereof, inorganic particles, metallic particles, or microcapsules.

When particles are allowed to disperse in a dispersion media, the dispersion medium may be water, alcohol, ether, and other various organic compounds, end various materials constituting material substances and living bodies.

There is no need to say that in microprocessing according to the invention, it is not always essential to use the above-mentioned laser trapping.

When it is to be applied to substrate surfaces other than particles, it is not indispensable to adopt such phototrapping means. Trapping methods using magnetic fields and electrical fields other than trapping by use of light may be employed as necessary.

When the energy of processing laser is controlled to cause laser multiphoton reactions for fine modification and microprocessing, said laser multiphoton reactions can be controlled only through the variation in energy of single laser, and also it is possible to maintain more selective control over energy in a multiphoton reaction by radiating two or more laser beams of different wavelengths.

For example, it is possible to radiate 355 nm light, a triwave of $Nd^3$ : YAG laser, to a multiphoton reaction while controlling the energy.

In the case of this laser multiphoton reaction, it is possible to:

1) make a hole in a silicon wafer, as fine as sub-micron order for dynamic RAM;

2) create carbon fiber and other conductors on polymers, organic matters and other non-conductors in an ultrafine manner by a photochemical reaction;

3) create a waveguide path by causing a change in refractive rate in polymers due to ultrafine thermal conversion; and, 4) create a memory in magnetic substances by causing changes exceeding curie temperatures in an ultrafine manner.

Some embodiments will be shown to further describe microprocessing and the device therefor.

Embodiment 1

In a construction of the device as indicated in FIG. 1, polymethyl methacrylate (PMMA) latex particles are trapped and irradiated by pulse laser for the reforming and local conversion of particles.

The diameter of PMMA particles at this time was approximately 5 to 10 $\mu$m.

1064 nm (CW) and 355 nm (pulse) laser beams from Nd:YAG laser as indicated in FIG. 1 were allowed to enter a microscope, and particles were trapped with the 1064 nm (CW) laser beam, and PMMA particles were processed with the 355 nm (pulse) laser beam.

Figure 2A:
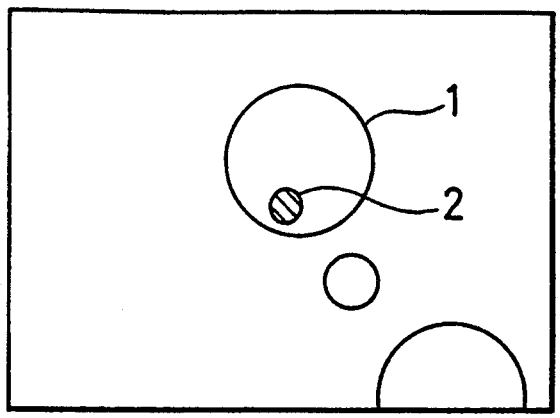
FIGS. 2 (a), (b) and (c) are drawings illustrating the states of particles through the radiation of laser beams which indicate embodiments of the invention.
Figure 2B:
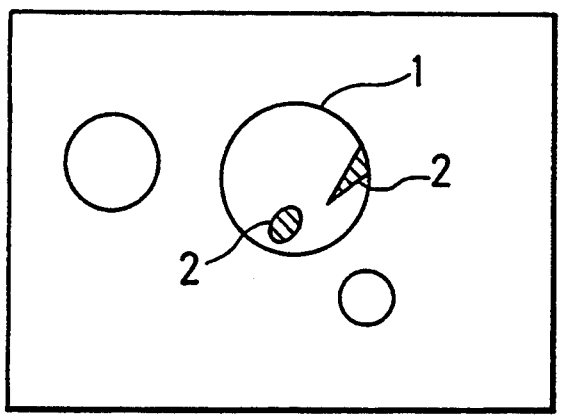
Figure 2C:
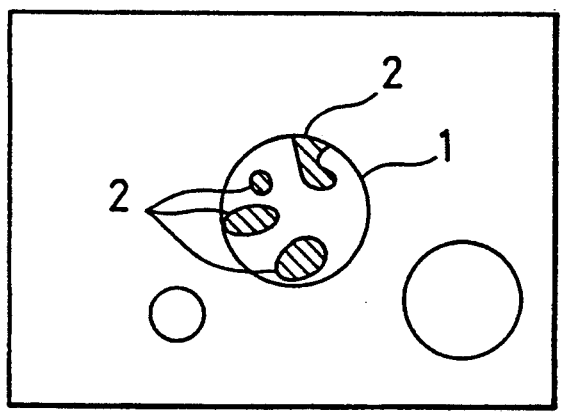

FIGS. 2 (*a*), (*b*) and (*c*) indicate the status of particles in a single, a two-time and multiple shots of pulse light. In the particle (1) trapped, a processed portion (2) is generated presumably due to the fact that PMMA crosslinking is severed, and the processed portion (2) is expanded by multiple shots. Ablation at 1 Hz is shown.

The result shows the possibilities of trapping, and the modification and processing of particles, with laser, and it is expected that the laser beam will find more applications when used with multiple kinds of particles.

Embodiment 2

Table 1 shows the laser trapping made using the fundamental wave (1064 nm) of cwNd$^3$ :YAG laser. It shows that the refractive index of polystyrene latex, PMMA latex, liquid paraffin droplets and other particles is larger than that of the medium surrounding thereof, they are trapped as are indicated by the principle. However, it could be observed that in the water droplet in liquid paraffin, the relationship of refractive index is inverted and water droplet is crawls out of focus of the laser. When the diameter of particles was larger than a laser spot ($\sim 1$ $\mu$m), they could be trapped three-dimensionally, but when their diameter was smaller than the laser spot, the force exerted in the direction of laser light axis (Z axis) became exceedingly small. In such a case, the particles could be manipulated two-dimensionally on a glass plate at the bottom of the sample cell. Though the particles of oxidated titanium were not spherical, they could be trapped two-dimensionally.

TABLE 1

Laser Trapping of Various Particles

| Medium (Refractive Index) | Particle (Refractive Index) | Trapping |
|---|---|---|
| Water (1.33) | PMMA Latex (1.49) | Yes |
| | Polystyrene Latex (1.59) | Yes |
| | Toluene Droplet (1.50) | Yes |
| | Liquid Paraffin Droplet (1.46~1.47) | Yes |
| | Titanium dioxide | Yes |
| | Salmonella Typhymurium | Yes |
| Ethylene glycol (1.43) | PMMA Latex (1.49) | Yes |
| | Polystyrene Latex (1.59) | Yes |
| Diethylene glycol (1.45) | PMMA Latex (1.49) | Yes |
| | Polystyrene Latex (1.59) | Yes |
| Liquid Paraffin (1.46~1.47) | Water Droplet (1.33) | No |

Embodiment 3

Figure 3A:
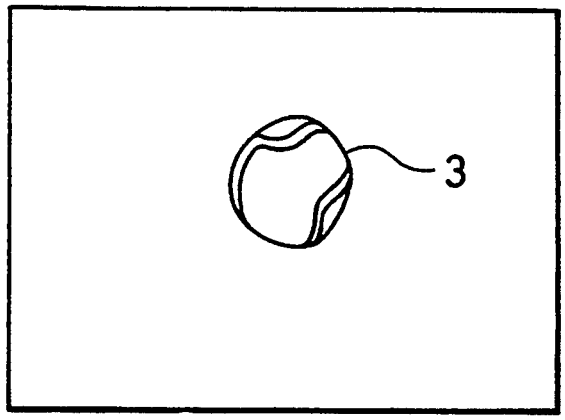
FIGS. 3 (a), (b) and (c) are drawings illustrating the states of implosion of a microcapsule as embodiments of the invention.
Figure 3B:
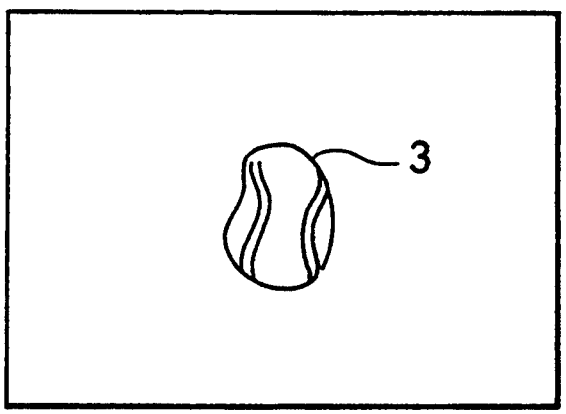
Figure 3C:
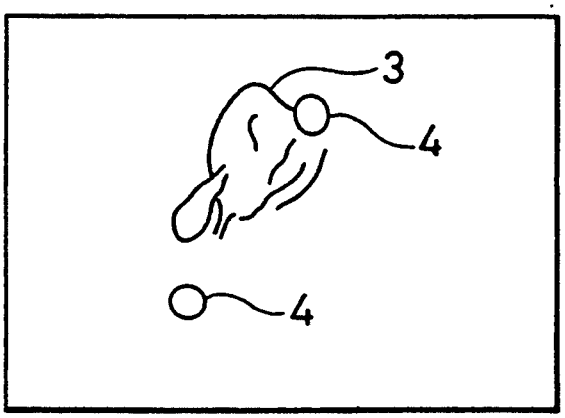
Figure 4:
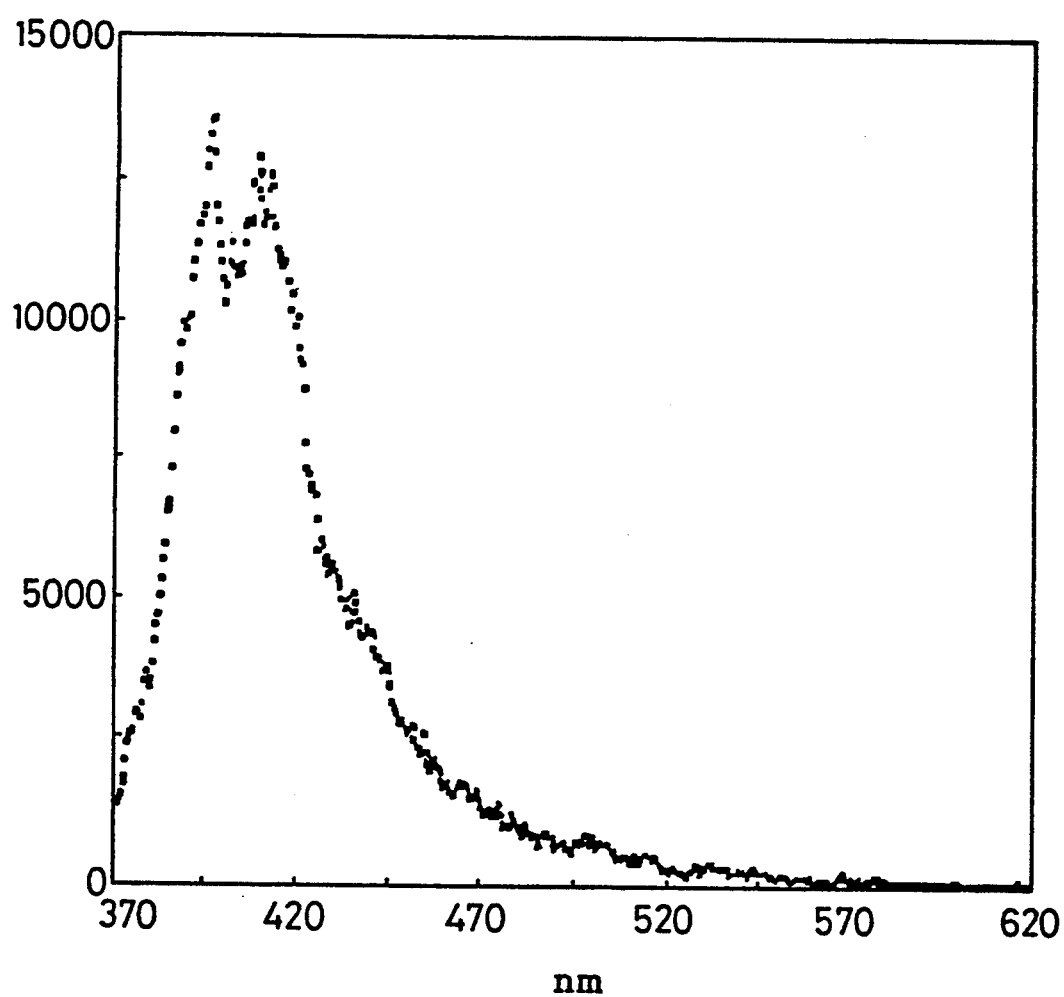
FIG. 4 is a measurement spectrum drawing by microscopic spectroscopy of this invention.

After non-spherical microcapsules with a diameter of 10 $\mu$m were trapped with laser, a pulse laser (355 nm, 7 ns fwhm) was radiated and caused implosion. The results are shown in FIGS. 3. FIG. 3 (a) indicates the state where the microcapsule (3) was trapped with laser. The strength of laser light entered for the trapping is 3.2 W. It was confirmed that this microcapsule (3) was trapped three-dimensionally by shifting the stage of a photomicroscope. FIG. 4-b indicates the state after 41.7 J/cm$^2$ of pulse laser was radiated on the microcapsule (3) trapped in a single shot. Though no implosion of the capsule was observed, it can be confirmed that the capsule was transformed with the radiation of pulse lasers. In addition, when 1.37 kJ/cm$^2$ was radiated in a single shot, an implosion of the capsule (3) occurred, and the toluene solution (4) in a pyrene of content solution was ejected into the outer water phase (FIG. 3-c). It was found that at that time, the toluene solution (4) ejected into the water phase is spherical and that this is trapped with laser.

Using this technology, a microcapsule in which a reaction group is contained is transported to a given place of an electrode subjected to fine processing, and only spatial region at and near the electrode as small as micron order can be chemically modified by the radiation of another exictation laser light.

Also, a microcapsule with anticarcinogen or other medicine enclosed is guided to a specified location in the living body, Embodiment 4

A laser beam was radiated on polymethacrylate (PMMA) for fine processing.

At this time, a pyrene had been doped in the PMMA.

Md$^a$*YAG laser K triple wave 355 nm (pulse) light was radiated, and a fine hole having a diameter of 0.5 $\mu$m and a depth of 5 $\mu$m was generated by laser ablasion.

The strength of radiation of laser beams is less than approx, 10 J/cm . By controlling this energy more accurately in connection with the restriction of laser beams, it becomes possible to obtain modification and processing in sub-micron order with much higher precision.

Embodiment 5

In a construction as indicated in FIG. 1, the latex used to dope the pyrene was trapped, and subjected to the radiation of pulse laser for the excitation of the particles.

The diameter of the particles of PMMA at this time was approx. 5 to 10 $\mu$m.

1064 nm (CW) and 355 nm (pulse) low-energy laser beams from the Nd:YAG laser were entered into a microscope, the particles were trapped with the 1064 nm (CW) laser beam, and the particles were excited with the 355 nm (pulse) laser beams.

It becomes possible to trace the time-resolved spectrum and reaction species from the light emission due to this excitation.

FIG. 4 indicates the spectra of the wavelength and strength of the emitted light.

The result shows the possibilities of trapping and spectrochemical analysis with laser, and its application as particle analyses is expected to expand.

Figure 5:
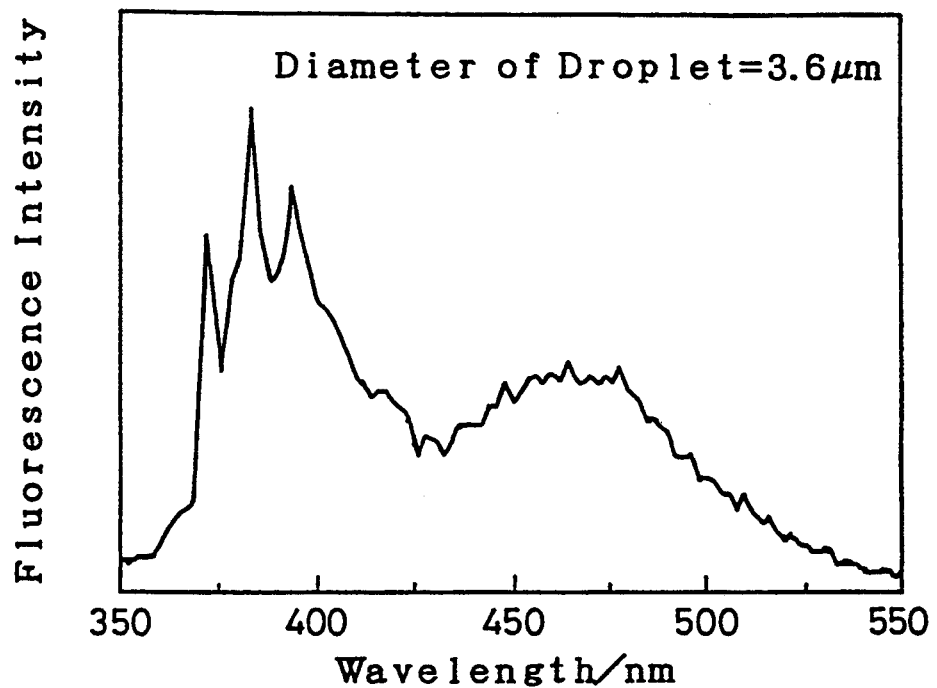
FIG. 5 is a plot depicting fluorescent intensity vs wavelength for a fluorescent pigment, in accordance with the process of the present invention.
Figure 6:
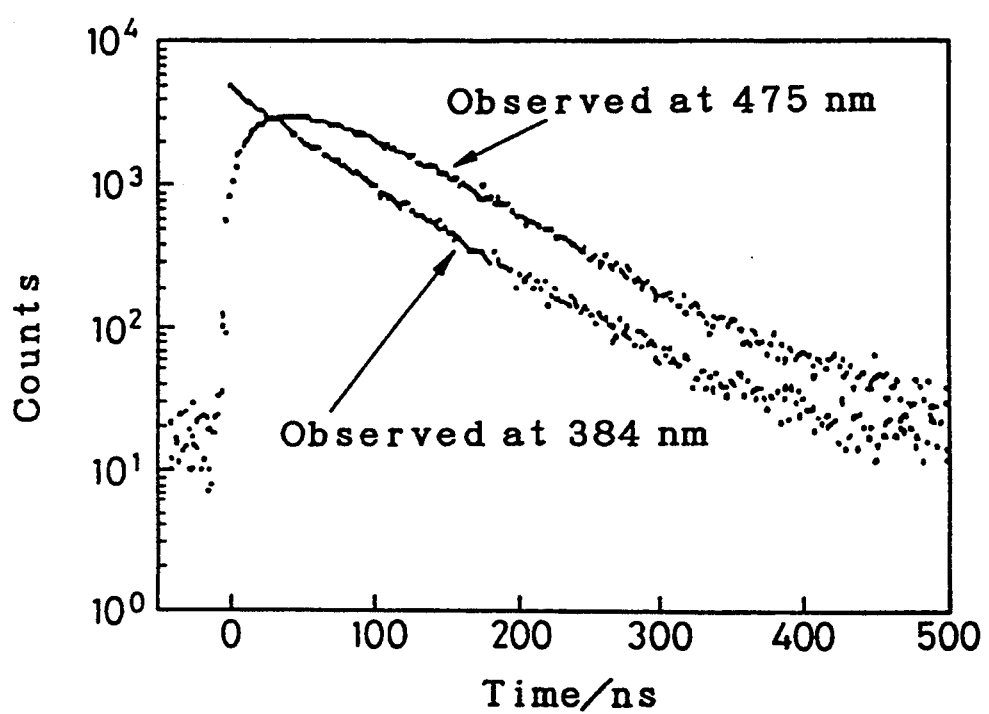
FIG. 6 is a plot of counts vs time at two given wavelengths for the process in accordance with the present invention.

Liquid paraffin solution ($1 \times 10^2$ mol dm$^9$) of pyrene was allowed to disperse in water, and the fluorescent light of the microdroplet thereof was measured. The results obtained by putting the 3.6 $\mu$m droplet to laser trapping and spectrochemical analysis were shown in FIGS. 5 and 6. The figures showed that the fluorescent spectrum was found to indicate the vibrational structure peculiar to the pyrene in the vicinity of 370 and 400 nm, and the band of excimer having its maximum wave in the vicinity of 470 nm, and also that it was possible to identify trapped particles. Moreover, the damping and rise was able to be observed. Similar measurements could be observed in a polymer latex in which a pyrene, p-terphenyl, and other fluorescent pigments ape doped.

We claim:

1. A process for making fine modifications in particles which comprises subjecting said particles to a multiphoton reaction with a laser.

2. The process according to claim 1 wherein said reaction is performed by variations in energy of a single laser or the radiation of multiple wavelengths and by control of the energy thereof to achieve said fine modifications.

3. A microprocessing device for modifying and processing particles or microcapsules which comprises a trapping laser and a processing laser.

4. A spectral device comprising a trapping laser and an excitation pulse laser.

* * * * *